United States Patent [19]

Manikas et al.

[11] Patent Number: 5,286,488
[45] Date of Patent: Feb. 15, 1994

[54] METHOD FOR TOPICAL TREATMENT OF LESIONS ASSOCIATED WITH VIRAL INFECTIONS

[76] Inventors: John T. Manikas, 2277 Fair Oaks Blvd., #400, Sacramento, Calif. 95825; Lawrence R. Manning, 7409 24th St., Rio Linda, Calif. 95673

[21] Appl. No.: 916,600

[22] Filed: Jul. 20, 1992

Related U.S. Application Data

[63] Continuation of Ser. No. 482,069, Feb. 16, 1990.

[51] Int. Cl.⁵ .............................................. A61K 35/78
[52] U.S. Cl. .................................. 424/195.1; 514/934
[58] Field of Search ...................... 424/195.1; 514/934

[56] References Cited

U.S. PATENT DOCUMENTS 4,525,344  6/1985  Tutsky ................................... 424/73
4,784,849  11/1988  Tutsky ................................... 424/73

Primary Examiner—John W. Rollins
Attorney, Agent, or Firm—Hana Dolezalova

[57] ABSTRACT

The use of the active ingredient present in the juice obtained from the green hull of the kukui nut for use as an antiviral pharmaceutical agent. This active ingredient is particularly useful in the topical treatment of viral infections, such as herpes simplex, genital herpes, genital warts, herpes zoster and chickenpox. The raw liquid juice, or the juice formulated in a pharmaceutically acceptable carrier, is topically administered to the surface lesion caused by the virus. Some components present of the active ingredient in the kukui nut hull juice include methyl esters of long chain fatty acids and their isomers.

4 Claims, 2 Drawing Sheets

METHOD FOR TOPICAL TREATMENT OF LESIONS ASSOCIATED WITH VIRAL INFECTIONS

This is a continuation of copending application Ser. No. 07/482,069 filed on Feb. 16, 1990, now allowed.

BACKGROUND OF INVENTION

1. Field of the Invention

The present invention relates to the use of the active ingredient obtained from the green hull of the kukui nut as an antiviral agent, particularly for use in the novel treatment of viral infections, in particular herpes simplex type 1 and 2, herpes zoster, genital warts and chickenpox.

2. Description of Related Art

Viruses are smallest of parasites but biggest nuisance the human population encounters on daily basis. Viruses are intracellular molecular particles with a central core of nucleic acid and an outer cover of protein. For their reproduction, viruses are wholly dependent on the host cells.

Several hundred different viruses are know to cause infection in man. Because of their wide prevalence, they create important medical and public health problems. Included among them is the most common of all viral diseases, the cold often accompanied by cold sores, which alone is responsible for one billion episodes of disease every year in the United States alone. Also included are such highly infectious viral diseases as measles, chickenpox, very painful and unpleasant herpetic viral diseases caused by herpes simplex or herpes zoster and such deadly viral diseases as rabies. All these viruses are spread quickly by man himself, mainly via respiratory and enteric excretions or by contact. Moreover, some of the viruses are very resistant and persistent and some of them, for example herpes simplex viruses, once inside the body they never leave.

There is no simple treatment of viral diseases. They are not susceptible to antibiotics and there is no other available treatment of viral diseases other than by chemotherapy which inhibits viral replication in the host cells. *The Merck Manual,* 170 (1982). Examples of these chemical agents are idoxuridine (IDU) useful for treatment of herpes simplex keratitis and methisazone active against influenza A virus. The other known viral replication inhibitors are acyclovir, ribavirin, vidarabine, gancyclovir and adenine arabinoside (ARA-A). These, and other viral replication inhibitors, however, are known to be cytotoxic, hepatotoxic, neurotoxic, nephrotoxic and having teratogenic effect, i.e., causing birth defect. *Virus Diseases,* 1-6 (1978) Crown Publishers, N.Y.

Thus it would be highly desirable to have available a nontoxic, preferably naturally occurring material which would be effective against viruses in general and against those viruses which are most painful, uncomfortable, ungainly and debilitating, such as herpes simplex and herpes zoster.

Herpes simplex, also called fever blister and cold sore is one of the most prevalent viral infection. The infecting agent is the relatively large herpes simplex virus herpesvirus hominis (HVA). There are two HVH strains. Type-1 strain commonly causes herpes labialis located on a lip, and keratitis, an inflammation of the cornea. Type-2 is usually located on or around genital area and is generally transmitted primarily by direct contact with herpetic sore or lesions. Thus, herpes simplex virus type-1 occurs above the waist and herpes virus type-2 occurs below the waist.

Estimated frequency and location of oral (herpes simplex type-1) and genital (herpes simplex type-2) infections are about half million of primary cases of type-1 per year, with 98 million of recurrent cases per year in the United States alone. Of the genital type-2 cases, there are around 500,000 cases of primary genital herpes with 3-9 million of recurrent cases per year in the United States. *Living With Herpes,* 1-11, (1983), Doubleday and Company, N.Y.

Herpes simplex infection is recurrent infection characterized by the appearance on the skin or mucous membranes of single or multiple clusters of small vesicles, filled with clear fluid on slightly raised inflammatory bases. These symptoms usually accompany a flu or some such other state where the body resistance is low. Herpes simplex is very infectious and it is rapidly and easily transferable by contact.

Herpetic lesions may appear anywhere on the skin or mucosa, but are more frequent about the mouth, on the lips, on the conjunctiva and cornea, and on or around the genitalia. Following a short prodromal period of tingling discomfort or itching, small tense vesicles appear on the erythematous base. Single clusters vary in size from 0.1 to 1.5 cm. The vesicles persist for a few days, then begin to dry, forming a thin yellowish crust. Healing is long and usually begins 7-10 days after onset of the viral infection and is complete by about 21 days. Healing may be slower, with secondary inflammation, in moist body areas. Individual herpetic lesions usually heal completely but recurrent lesions at the same site may cause atrophy and scarring. It will be appreciated that the herpes simplex outside or inside mouth, lips, cheeks, chin and particularly on or around the genitalia is very painful and uncomfortable as it burns or itches, as well as ungainly, with an often open sore on the lip and, particularly as it does on recurrence, leaving the ugly lesions on or around lips.

As pointed out above, once present the virus herpes simplex never leaves. Although at about three weeks of herpes simplex infection the evidence of infection is no longer manifest, the virus has not been eradicated from the body; rather it remains in a dormant state in nerve tissue near the site of infection. In the case of oral, labial and facial herpes, the latent virus takes up residence in a nerve cluster called the trigeminal ganglion, located near the cheek bone. There are two factors that are important in viral reactivation—general health and stress. Since the medical science has not come up yet with a substance which is fully curative, the body is left on its own in limiting the viral activity. And of course, in organism weakened by ill health, infection, stress and other circumstance, the recurrence of herpes simplex viral infection is a serious problem. Moreover, once a virus takes over and develops into full fledged sore, it runs its course, submitting the victim to pain, itch and scarring connected with viral sores.

Thus, it would be very appreciated by the herpes virus carriers and victims, if there would be available non-toxic, but highly effective antiviral agent which would be able to suppress and alleviate immediately the first symptoms of the viral infection, i.e., swelling, tingling and itching which occurs on the site of sore before it develops into full fledged blister, and thus prevent the development of sore which could last up to three weeks and has high probability to leave a scar. Such agent would not only have appreciable therapeutic effect by inhibiting the development of painful sore of the individual but also prophylactic effect by terminating an infection spread to other people caused by highly transmittable stage of virus when blisters erupt and can easily be transmitted by air or on contact.

The type-2 of herpes simplex has even bigger and more severe, if possible, consequences. Due to its location on or around the genital area, the social stigma attaches of having this type of herpes infection categorized as a venereal disease. The viral disease itself is much the same as the herpes simplex type-1. Initial and recurring attacks, similar but probably more severe than those of type-1, occur in the neighborhood of the genital organs. The initial attack begins with swelling, reddening, and pain in the area surrounding the site of infection with the inflammation developing and extending over the whole groin, thighs and buttocks. This is accompanied by a low-grade fever, mild flu-like symptoms and swelling of the lymph glands in the groin. The development of small, blister like sores soon follows over much of inflamed area rapidly becoming grayish yellow and ulcerous. These blisters typically last for about two weeks. The symptoms in recurrent episodes are generally not so severe but nonetheless unpleasant and uncomfortable. The recurrence may occur as often as several times a month.

Aside of its high infectivity and painful and humiliating conditions, genital herpes pose the serious problems to infants born to infected mothers as such infants may become infected during birth. Another serious problem is the supposition that genital herpes in women may lead to cervical cancer. Moreover, as with the type-1 herpes simplex virus, in case of genital herpes, the virus lies dormant in the sacral region, located outside the spinal canal. *The Herpes Book*, 1–13 (1980), J. P. Tarcher, L.A.

Treatment of genital herpes is primarily by systemic administration of antiviral drugs as described above, for example by IDU and trifluridine (TFT) with all dangers connected with their high cytotoxicity, with ARA-A, another antiviral with somehow lesser toxicity, and acyclovir or bromovinyldeoxyuridine which are both enzyme inhibitors semi-specific to virus replication. All these agents are given primarily systemically and have high probability to cause severe side effects, as discussed above. Moreover, none of these agents is a selective inhibitor of only the herpes simplex virus replication but effects also a replication of normal cells. Therefore, when used in doses large enough to seek and destroy all the active herpes viruses dormant in the sensory ganglia, these compounds may also be highly disruptive to the normal DNA in the host cells in which the virus multiplies. This is highly undesirable effect since the replication of normal cells is also effected. The topically administered acyclovir ointment seems to be effective in the treatment of primary first occurrence of genital herpes infection but has little if any, effect on recurrent genital herpes disease.

Thus, it would be advantageous to have available treatment of genital herpes which would prevent development of painful sores and inflammation in the genital area, prevent their recurrence and yet be innocuous enough toxicologically so that no systemic administration of cytoxic chemical substances is necessary or needed.

Yet another form of viral herpes disease is so called herpes zoster, commonly known as shingles. Herpes zoster is a disease of middle or old age characterized by extreme pain in a limited area of the upper body or face and an outbreak of small pimply blisters in the same area usually along the nerve branches. The herpes zoster is caused by varicella-zoster virus, the same virus that causes chickenpox. Herpes zoster is an acute central nervous system infection involving primarily the dorsal root ganglia and characterized by vesicular eruption and neuralgic pain in the cutaneous areas supplied by peripheral sensory nerves arising in the affected root ganglia in which the inflammatory changes occur.

There is no specific therapy to this extremely painful viral infection. Corticosteroids, if given early, may relieve pain in severe cases. Aspirin and other anti-inflammatories or antiviral agents systemically may alleviate the pain. However, these agents have the same undesirable side effects as discussed previously.

Thus, it would be extremely important to find an agent which would alleviate the pain connected with the symptomatically occurring blisters during herpes zoster attack.

Another viral infection which may severely effect the patient in that it disfigures patient's face is varicella also know as chickenpox caused by varicella virus. This is a rare form of chickenpox in which the eruption leads to a gangrenous ulceration. There is severe scarring (pock marking) following the healing of the ulceration which never disappears and the person's face is forever disfigured. Moreover, there is no treatment known or prevention for the chickenpox or the subsequent scarring.

Consequently, it would be desirable to have available treatment and/or prevention for the gangrenous ulceration before it results in the scars.

Another highly unpleasant and painful conditions are genital warts caused by human papillomavirus (HPV). Not only this condition is unpleasant and painful but it may also contribute to cervical and genital cancers.

Thus, it would be advantageous and highly desirable to provide an effective treatment against genital warts.

The herbal medicine and use of various extracts or portions of plants as curatives for various diseases has been practiced for thousands of years. For example, quinine, an extract from the bark of a tropical tree, was found to be effective and is still used to mitigate the symptoms associated with malaria.

Long before the introduction of modern scientific methods for development of sophisticated therapeutic agents, remedies and treatments were sought for viral diseases, in particular for painful, distressing and recurring lesions of herpes. The common remedies and treatments had a basis in herbal medicine or folk practices and were usually topical preparations applied directly to the sores to relieve pain, itching, oozing, and discomfort. Such remedies as boiled cloves, tea leaves, peppermint oil, clove oil, eucalyptus oil, paste made from cornstarch, honey, slippery elm, comfrey root, myrrh or volcanic ash, cactus sap and milk compresses were among the many concoctions employed to relieve the symptoms of the disease. For the most part, these agents would afford a certain measure of relief where there was none before. None of these agents however, was successful in decreasing the number of recurrence of sores and in completely suppressing the herpetic symptoms. *The Herpes Book*, 149 (Supra).

It has now been discovered that the active ingredient present in the liquid obtained as a raw material or as an extract from the green hull of the nut of the kukui tree has a very potent and specific antiviral activity which results in extremely fast suppression of initial symptoms if administered before breakout and has an extremely potent healing activity if administered during the breakout. Following the administration of the active ingredient to the patient suffering from viral sores, the healing period of the sore is shortened from 14 to 21 days to 1-2 days when all painful symptoms disappear, to 3-4 days when all signs of breakout are gone.

Kukui nut tree, *Aleurites moluccana*, also known as candlenut tree, is a native tree in all countries from western Polynesia to southern Asia an is generally found in woods of lower mountain zone, web gushes and valleys, ravines and hanging valleys of tropics and subtropics. In the United States, the kukui tree is found in all islands of Hawaii.

Certain medicinal and other uses of various portions of the kukui nut tree or its nut have been reported, and in particular in native Hawaiian medicine, the kukui nut had many uses. Uncooked kukui nut kernel was used as a laxative and a diuretic. Baked kukui nut kernel in various preparations was used for the treatment of wounds, ulcers, sore throat and asthma. The smoke of the kukui nut shells was even used to reduce the size of a swollen womb. The recipes of a few of the early herbal remedies using kukui nut tree products have been recorded and preserved.

Specifically, the *Hawaii Dental Journal*, pages 8 and 13 (1986), discloses several uses of kukui nut tree. Kukui flowers, baked kukui nut and sugarcane mixture was used for stomachache and bowel disorders. Kukui bark was used for herbal tea. Chronic ulcers and scrofula were treated with mixture containing kukui meat and kukui nut cooked in kukui leaves. Sap from the kukui nut tree was used to treat bad breath and coated tongue. The juice of the kukui fruit was used as a mouthwash, for the treatment of a fungal infection thrush or moniliasis—and for other superficial internal oral lesions. To collect the juice (sap), the still green fruit was separated from the stem, and a small amount of clear juice which appeared where the stem had been attached, was collected and combined with the juice from several kukui fruit and then used by dipping a finger into the juice and applying it to the oral lesion. While the juice clearly has the astringent properties, the chemical composition of the juice is as yet unknown and its effects on oral fungal infections is still unknown and has not been studied or quantified.

Additional references of general interest include the following:

June Gutmanis, *Kahuna LA'AU LAPA'AU*, 24-26, 30 and 36, published by Island Heritage, Honolulu, Hawaii (1976).

*Hawaiian Herbs of Medicinal Value*, translated by K. Acana in 1972.

All of the publications cited and/or described herein are expressly incorporated by reference and made part of this application.

While the certain therapeutic properties of the juice of the kukui nut hull are known, there has been no reports or suggestions regarding the use of the active ingredient present in the juice from the green hull of kukui nut to treat general viral infections, such as herpes simplex, herpes zoster, genital herpes, genital warts, chickenpox, or the like.

The present invention discloses until now unknown therapeutic and prophylactic effect of the active ingredient present in the kukui nut hull extract and a composition therefor for treatment of viral infections.

SUMMARY OF INVENTION

One aspect of the present invention relates to a pharmaceutical composition comprising the active ingredient present in the raw liquid juice or extract obtained from the slightly immature green hull surrounding the nut of the kukui nut tree, which is also known as *Aleurites moluccana* and its use in preventing development of, treating, ameliorating or curing viral infections.

Another aspect of the present invention relates to an extraction method to recover the juice of the still slightly immature kukui nut hull and it use as raw material or in admixture with pharmaceutically acceptable excipients.

Still another aspect of this invention relates to the determination of the chemical identity of the active ingredient present in the raw juice or in the chemical extract obtained from the immature kukui nut hull.

Yet another aspect of the present invention relates to a method of systemic or topical treatment of viral infections such as herpes simplex, genital herpes, herpes zoster, genital warts or chickenpox using the raw juice or extracted juice from the hull of the kukui nut.

DETAILED DESCRIPTION OF THE INVENTION

Definitions

As used herein:

"Kukui" refers to the tree *Aleurites moluccana* also known as the candlenut tree.

"Hull" or "husk" refer to the hard green covering, about ¼ inch thick when immature, of the kukui nut.

"Sap", "juice", "liquid" refers to the watery liquid found in the immature hull or husk of the kukui nut.

"Viral infection" refers to all types of infections caused by viruses including but not limited to herpes simplex, genital herpes, herpes zoster, chickenpox or genital warts.

"Pharmaceutically acceptable excipients" means any and all additives which are acceptable in the pharmaceutical sciences, and may be a high molecular weight polymeric agents such as cellulosic polymers hydroxyethylcellulose, hydroxypropylcellulose, methylcellulose, vinylic polymers polyvinylpyrolidone, polyvinyl alcohol, polyethylene glycol, talcum or other additives or binders.

"Active ingredient" or "active agent" means the material present in the raw liquid or in the chemical extract obtained from the green hull 30 of the kukui nut tree and maybe yet unknown individual chemical compound or compounds or combination thereof, or it may be a combination of all fatty acids, as shown in the obtained spectra alone or in combination with the unknown active ingredient.

Figure 1:
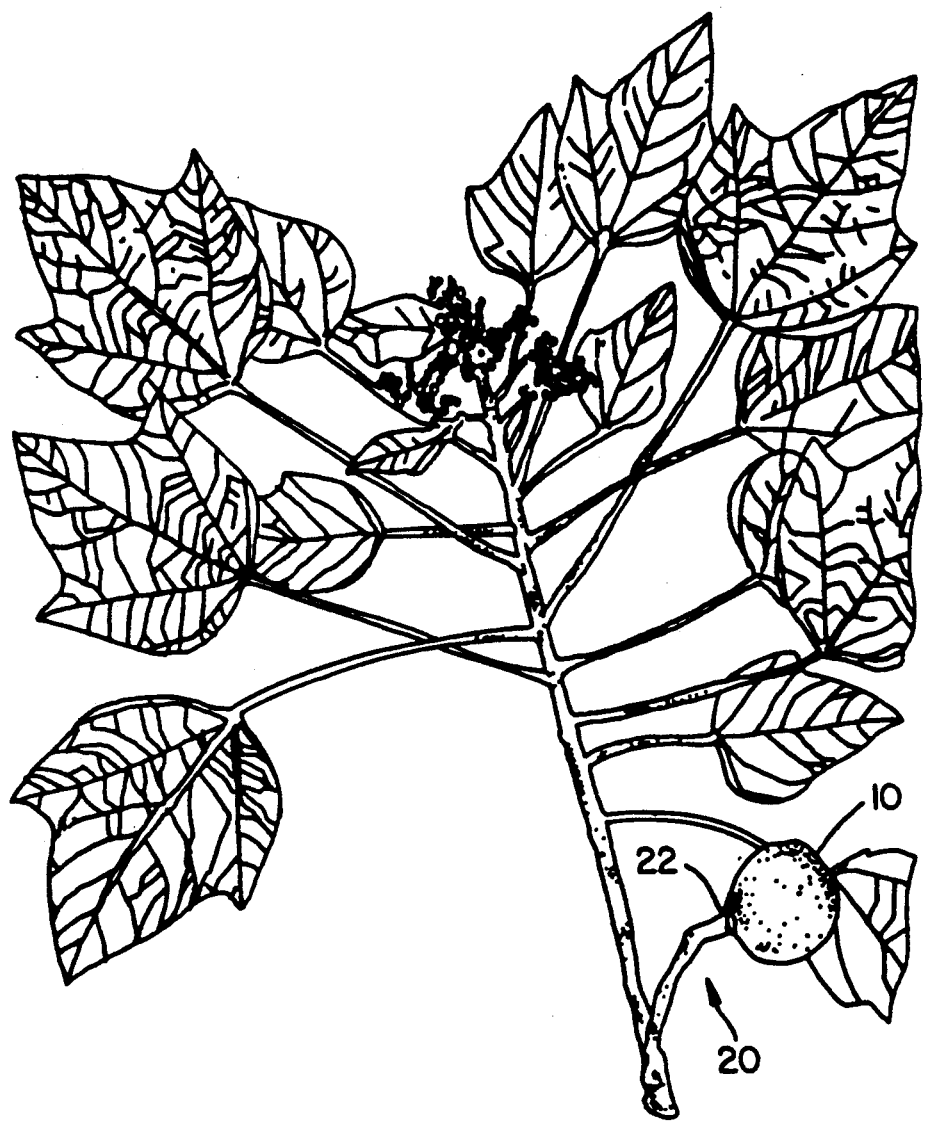
FIG. 1 depicts the drawings of a branch of kukui nut tree showing stem, leaves, flower cluster and fruit.
Figure 2:
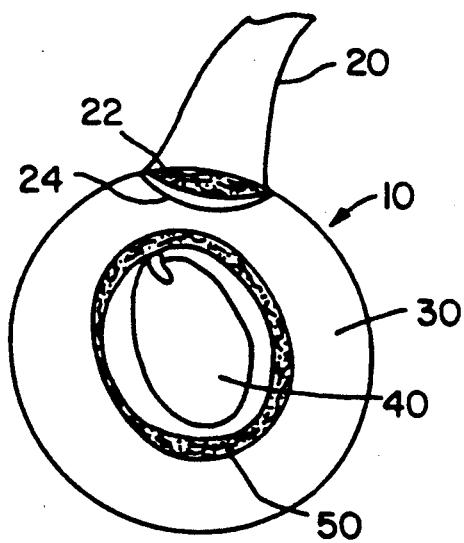
FIG. 2 shows the drawing of the kukui nut tree fruit-drupe or nut.

The branch of the kukui nut tree is shown in FIG. 1, showing the position and attachment of the kukui nut 10, through the stem 20. Stem attaches to the nut at point 22. When the stem is removed, the bowl-like opening 24 remains in the nut hull, as shown in FIG. 2.

Kukui is tall tree bearing as its fruit "drupe" or nut containing a seed 40. The nut 10 is 1½-2 inches of size.

The nut is covered with nut shell 50. Outer part of fruit consist of hard, green covering, a hull 30, about ¼ inch thick when immature. *Ethnobotany of Hawaii*, 137 (1974) University of Hawaii, Honolulu, Hi.

The active ingredient is obtained from the hull of the immature nut of the kukui nut tree. The outer part known as hull or husk 30 of the nut 10 of the kukui nut tree consists of a hard green covering, usually about a quarter of an inch thick when the nut 10 is immature. When the nut is mature, this green hull turns a dark grayish-black and softens, especially after the fruit has fallen. In fact, this darkened hull portion of the nut decays rapidly under the usual conditions in which this tree grows.

The raw material and/or extract obtained from the hull contains an active ingredient having potent antiviral activity and may be used either in its raw form or chemically extracted form. When properly protected against spoilage by storing it in the dark glass vial at room temperature or refrigerated at 4° C., preferably at room temperature, it is usable for extended period of time. Properly preserved material has stability for about 2 years without a decrease in its antiviral activity.

The active ingredient containing material may be formulated in any kind of pharmaceutically acceptable form such as injections, tablets, capsules, drops, ointments, creams, sprays or soaps.

The active ingredient is collected from the nut of the kukui nut tree which grows commonly in the Hawaiian Islands or in other tropic or subtropic climate.

The collecting of kukui nuts for the purposes of this invention was done on Kona in the Hawaiian islands, where these trees are widely spread. There is one season for nut collection, lasting from October to December. The nuts for the purpose of this invention are collected before the nut becomes fully mature, i.e., at the end of November.

The hull of each nut provides approximately 1–2 drops (10 ul/drop) of juice. Consequently several hundreds nuts need to be collected to provide measurable amount of raw material. These not yet completely mature kukui nuts, i.e., still with a green hull intact, are collected from the kukui nut trees and it is important to cut nuts from the trees in such a way that the stem of the nut stays intact. Nuts are then brought to the laboratory and further processed.

In the laboratory, nuts 10 are washed, still with stem 20 intact and positioned in the multiple laboratory tubes stand so that the nut's bottom sits in the stands opening and the stem 20 is facing up. Then, the stem 20 is gently pulled from the nut. The removal of stem 20 leaves a small bowl-like opening 24 in the green hull 30 into which opening 24 a yellowish-brown viscous liquid seeps from the nut hull 30. This liquid is carefully collected by aspiration with a sterile aspirator or by any other means and transferred into dark brown glass vial prewashed and sterilized. Generally, one to two drops is obtained from each nut and from 50 nuts between 0.5 to 1 milliliter of active antiviral kukui nut agent is obtained. Then, the vial is closed, sealed and stored until clinically used or formulated.

The stability of the active ingredient was determined by storing the sealed container in the different temperature conditions and testing the biological antiviral activity in one months intervals. Under temperature conditions from the room temperature to about 4° C., the active ingredient containing liquid without any preservation material had a shelf life and antiviral activity preserved for approximately two years. Upon storing at a refrigerator at 4° C., the liquid solidifies and may change considerably but preserve its antiviral activity.

The extraction of active antiviral agent from nuts of the kukui nut tree is done as follows. Several hundreds or thousand immature kukui nuts having the stem attached with a green hull intact are picked at any place where kukui nut grows. The stem is removed, discarded and the seeping liquid removed as described above. The whole nut is then immersed in the extraction organic solvent, preferably lower alcohol such as methanol, ethanol, propanol or butanol at concentration from 50–98% of, preferably in 95% ethanol for 2 hours to 7 days, preferably 1 day.

In alternative, the hull is carefully removed from each nut by cutting and scraping it from the nut shell 50 and broken up into small pieces no larger than about 0.1–0.25 inch. The pieces are then placed in a solvent extractor or beaker containing an organic extraction solvent, preferably 95% ethanol and extracted approximately into 150 ml of solvent for 2 hours to 7 days, preferably for 24 hours. The extractor container is continuously or occasionally gently shaken or rotated. The pieces of hull are then removed, solvent extracts is concentrated at room temperature under reduced pressure to 5 ml. A thick viscous yellow liquid is obtained as is, or it may be diluted, which has a potent antiviral topical activity with a shelf life at ambient temperature for about two years. The liquid may be formulated to drops, ointments, creams, sprays, injectables, tablets, capsules or to any other form. The preparations were used for clinical treatments as described in Examples 5–9.

The liquid in raw, diluted or concentrated form, of which the active antiviral ingredient is obtained from the green hull of the kukui nut, was used for preparation of drops, ointments, injectables, sprays, tablets, creams or other pharmaceutical formulations or for storage.

The concentrated form was obtained as follows. Five ml of the juice of the green hull of the kukui nut obtained by the above-described procedure is placed in a 10–50 ml round-bottomed flask. The flask is placed in a water bath at 20°–28° C. and a mild vacuum is applied under rotation for around 2 hours or until the residuum is about 1–3 ml. About 2 ml of volatile material is removed. The biological activity of the remaining concentrated liquid of kukui nut juice is determined. It has a pharmaceutical activity of about 1.6–5 times of the natural unconcentrated juice with the same shelf life of about 2 years. The concentrated liquid is stored at room temperature or in the refrigerator at 4° C., without any impairment in the biological activity. Care must be taken to keep the juice from becoming essentially a dry or semi solid slurry. Consequently, it is important that the only mild refrigeration and/or vacuum conditions are applied for extended rather than short time. Otherwise, the pharmaceutical activity may decrease significantly.

The antiviral activity of the active ingredient present in the raw liquid obtained form the kukui nut hull or in the chemical extract obtained from the kukui nut hull is formulated into various pharmaceutical formulation, as described above, or in some instances used nonformulated, i.e., in raw form.

Topically, the active ingredient is applied either in raw form, or as drops, ointments, sprays, creams or soap. Systemically, the active ingredient is combined with binders or stabilizers and other pharmaceutically acceptable materials to form tablets, capsules or injectables.

Patients are chosen from those having diagnosed primary and recurrent herpes simplex type 1 or 2, herpes keratitis, herpes zoster, genital warts or chickenpox.

Usually the method of treatment includes either the systemic or topical administration of the active ingredient obtained from the juice. Topically, the active ingredient is applied to the surface lesion of the virus in amount between about 10 to 500 ul between 1 and 3 times daily until the sore, lesion and accompanying discomfort abates and essentially disappears.

The systemic administration is via intravenous injection of properly formulated active material injected to patient suffering from viral infection in need of such treatment, in amount effective to abate the viral infection symptoms.

The systemic oral administration may be given to persistent cases of viral infection, in particular to patients with recurring expression of viral disease, such as herpes simplex type 1 or 2 or herpes zoster, for several days or until needed.

A process for obtaining an antiviral pharmaceutical agent composition, includes following steps: obtaining an immature green kukui nut(s) with its (their) hull and stem intact, washing the whole nut with stem, removing the stem and immediately collecting the liquid juice which exudes from the opening of the hull, and storing the collected liquid juice at ambient temperature to about 4° C. temperature, preferably at room temperature.

An additional process for obtaining the juice containing active agent from the green hull of a kukui nut for topical medicinal use includes obtaining and washing the outer surface of an immature kukui nut in its green hull, removing and collecting and concentrating the hulls of a multiplicity of kukui nuts, chopping the hulls to produce smaller pieces having an average diameter of about 0.1 inch or smaller, pressing these pieces at a pressure of between about 10 and 1000 pounds per square inch, and collecting the exudate liquid juice.

A further process includes extracting the hulls with an organic liquid, and concentrating the organic liquid to produce an oily yellow residue.

The following examples are to be interpreted as being representative and illustrative only. They are not to be construed to limiting the invention in any way.

UTILITY

This invention concerns a discovery that an active agent in diluted or concentrated form, whether pharmaceutically formulated or in a raw form, obtained from the hull of the kukui nut possesses highly effective antiviral activity. Such activity is in particular present when such agent is topically applied to the herpes simplex type-1 or type-2 sore. Clinical case listed in Examples 5 and 6 show that the treatment with the active ingredient of this invention is able to suppress a full development of painful sores, that it considerably and substantially shortens a period of healing from 14–21 days to 1–5 days at most, usually to about 2 days. That it is able not only to arrest the development of sore to the full blown open sore but also to decrease the number of reocurrences of the herpes simplex infection. Even such persistent cases as bimonthly or monthly recurrences were positively effected and the recurrence periods extended considerably. Opthalmic treatment of herpetic keratitis is also effective.

This invention is also useful for treatment of other viral infection, particularly those which are expressed topically as blisters forming painful chain localized along the nerve path appearing during the herpes zoster attacks, or genital warts caused by the viral infection. The rush appearing in chickenpox which often develop into ulcerous spread on the face is also reacting positively to the topical treatment which prevents a full development of ulcerous breakouts leaving deep scars on the face.

While the topical administration is preferred, the active ingredient of this invention is also active when administered systemically to treat persistent viral infections.

EXAMPLE 1

Collecting the Active Antiviral Agent from Kukui Nut

This example illustrates how the active ingredient is collected from the nut of the kukui nut tree which grows commonly in the Hawaiian Islands.

The collecting of kukui nuts wa done in Kona on the Hawaiian islands, where these trees are widely spread. There is one season for nut collection, lasting from October through November to December. The nuts for this study were collected at the end of November.

One hundred not yet completely mature kukui nuts still with a green hull intact were picked from the kukui nut trees. It was important to pick nuts in such a way that the stem of the nut stayed intact. Nuts were brought to the laboratory.

In the laboratory, nuts were washed, and positioned in the laboratory stand so that the stem was facing up. Then, the stem was gently pulled from the nut and from the hull. The removal of stem left a small bowl-like opening in the green hull into which a yellowish-brown viscous liquid seeped from the nut hull. This liquid was carefully collected by aspiration with a sterile aspirator and transferred into dark brown glass vial which was prewashed and sterilized. Generally, one to two drops was obtained from each nut. From 100 nuts between 0.5 to 2 milliliters of active antiviral kukui nut agent was obtained. Then, each vial was closed, sealed and stored under room temperature. Under these conditions, the raw material without any preservation agents had a shelf life and antiviral activity preserved for approximately two years.

EXAMPLE 2

Extraction of Active Antiviral Agent from Kukui Nut

This example illustrates the extraction of active antiviral agent from nuts of the kukui nut tree.

One hundred kukui nuts with a green hull intact from Kona in the Hawaiian Islands were picked having the stem attached. The stem was removed, discarded and the seeping liquid removed as described in Example 1.

The hull was then carefully removed from each nut by cutting and scraping and broken up into small pieces no larger than about 0.25 inch. The pieces were then placed in a solvent extractor containing 95% ethanol and extracted into 150 ml of 95% ethanol for 24 hours. The pieces of hull were then removed, alcohol extraction and the ethanol extract was concentrated at room temperature under reduced pressure to 5 ml. A thick viscous yellow liquid was obtained which had an antiviral activity with a shelf life at ambient temperature for about two years. The liquid was used in examples 5–9.

EXAMPLE 3

Concentration of the Kukui Nut Hull Juice

This example illustrates the concentration of the active antiviral ingredient obtained from the green hull of the kukui nut for preparation of drops, ointments, injectables, sprays, tablets, soaps, creams or other pharmaceutical formulations or for storage.

Five ml of the juice of the green hull of the kukui nut obtained by the procedure of Example 1 or 2 was placed in a 50 ml round-bottomed flask. The flask was placed in a water bath at 20° C. and a mild vacuum was applied under rotation for around 2 hours. About 2 ml of volatile material was removed. The remaining concentrated liquid of kukui nut juice had a pharmaceutical activity of about 1.6–2 times of the natural unconcentrated juice with the same shelf life of about 2 years. The concentrated liquid was stored in the dark glass vial at room temperature.

EXAMPLE 4

Pharmaceutical Compositions (a) The active agent of Example 1 was used as a raw material without further formulation as a topical pharmaceutical agent for viral infections and lesions.

(b) The active agent of Example 1 was used without further formulation in the treatment of herpes simplex, genital herpes, herpes zoster, genital warts or chickenpox.

(c) The yellow liquid of Example 2 was used without further formulation in the treatment of viral infections and lesions by topical application.

(d) The yellow liquid of Example 2 was used without further formulation in the treatment of herpes simplex, or genital herpes, herpes zoster, genital warts, or chickenpox by topical application.

EXAMPLE 5

Treatment of Herpes Simplex Type-1

This example illustrates the use of the current invention in early repression, amelioration and treatment of sores and blisters connected with herpes virus type-1 infection.

Topical ointment or raw liquid prepared and described according to Example 4 was administered to all patient cases listed below. Depending on the severity and advancement of the case the ointment was applied once or several times until all symptoms disappeared.

Case 1

Male patient with recurrent herpes simplex type-1 had, at day 1 an extensive, approximately 3–5 mm sore on lower lip. During previous occurrences, such sore lasted 10–14 days until completely healed. Following on treatment with a topical composition made of raw material applied as a thin layer by cotton swab, patient felt relief within 24 hours with sore barely visible and completely healed in another 24 hours.

Case 2

Female patient with initial swelling on the upper lips about to break, was administered a small amount of the raw liquid over the swollen lip with appearing sore. Within 24 hours, both swelling and the starting sore were gone without traces or lesion.

Case 3

A 25-year old well nourished caucasian male was diagnosed to have the viral infection herpes simplex type-1. The infection (open sore) was located on the patient's right lower lip and was about 2 centimeters in diameter. Two drops of the hull juice of Example 1 were placed on the infection site. Within 24 hours the p in from the site of the infection has disappeared, the sore has dried and diminished to be about 1 centimeter in diameter. Within 48 hours the surface sore has completely disappeared.

Case 4

A 21-year old black female was diagnosed as having herpes simplex type 1. The infection localized in the patient's upper lip covering the right side. It was about 1 centimeter time 3 centimeters wide. About 20 ul (2 drops) of the semi-solid concentrate of Example 3 was placed on covered the sore site. About 12 hours later, an additional 20 ul of the semi-solid was placed on the site. Within 24 hours the surface pain of the infection has disappeared. Within 48 hours the sore has dried completely and essentially disappeared.

EXAMPLE 6

Treatment of Herpes Simplex-Type 2

This example illustrates the use of the current invention in suppressing early symptoms of recurrence, in ameliorating and treatment of sores and blisters connected with genital infection caused by herpes simplex virus type-2.

Topical ointment or raw liquid prepared and described according to Example 4 was administered topically to all patient cases listed below. Depending on the severity and advancement of the case, the ointment was applied once or several times until all symptoms disappeared.

Case 1

Female patient 28 years old had herpes sore breakout of size of quarter on the left buttock for three days and was in extremely painful conditions prior to administration of single smear of the raw active agent of this invention. During the next 24 hours, the swelling and redness disappeared. Within 36 hours, the blisters dried to small blood clot covered regions, itching and pain all but disappeared.

Case 2

A 24 years old male with fresh outbreak of herpes blisters on shaft under head of penis was treated with ointment assuring that all blisters and swelled area was covered. Within 24 hours, the redness, swelling, itching and pain subsided. Blisters were dry and scabbed. In 48 hours all symptoms disappeared and there were no signs of the outbreak.

Case 3

A 34 year old male in otherwise good health was diagnosed in 1981 a having herpes simplex type 2. No prior treatment available at the time was effective to help the condition.

The patient was introduced to the active ingredient of this invention in 1983 during one outbreak of the virus. One to two drops of the juice were applied to the surface lesion every 12 hr. The first treated outbreak would subside and become less severe. The time between viral outbreaks which was originally in weeks, stretched with this treatment to one to several months. When the viral infection reappeared, it reacted promptly to 1-2 drops of the active agent applied topically.

Case 4

A 36-year old female was diagnosed as having genital herpes on or about 1978. No useful prescription was found to be available then or until the beginning of this treatment to mitigate the discomfort of the surface lesions of this patient. The patient had an average of four active reoccurrences of the surface genital herpes viral infection per year in 1986, 1987 and 1988. The patient was extremely uncomfortable with the burning and itching of the lesions.

In 1988, at the beginning of one reoccurrence, about 1-2 drops of the undiluted active ingredient (raw material) was applied using a cotton swab twice a day at about 12 hr intervals. Within the first 24 hr, the discomfort and itching decreased dramatically and almost disappeared. The 1-2 drops of active agent was reapplied at about 12 hr intervals. The surface lesion disappeared in three days. The sticky nut juice which dried quickly seemed to form its own medicated bandage having a topical anesthetic as well as therapeutic quality.

Case 5

A 25-year old male was diagnosed as having the herpes virus type-2 in 1985. After the application of 1-2 drops of the undiluted active agent, the pain and itching became less severe. The surface lesion dried up and disappeared in two days. The reoccurrence of the viral infection has been slowed down to one or two per year depending on patient's general health conditions.

Case 6

A 26-year old female was diagnosed in 1985 as having herpes virus type-2. The virus infection would appear about every month, usually a few days before the menstrual period occurred. After topical application in 1988 of 1-3 drops of active ingredient every 24 hr, the symptoms such as lesions, itching, and pain disappeared in less than 5 days and have not reoccurred.

Case 7

A 30-year old male had his first outbreak of genital herpes in 1981. The occurrence lasted six days. The virus would reoccur once or twice a month for the next three years. A small amount (1-3 drops) of the undiluted active ingredient was topically applied to the surface lesion. The topical application was continued every 24 hr, and the lesion dried and disappeared in three days or less.

Since the initiation of this treatment, this patient has had only about 3 or 4 occurrences of virus outbreak in the past 3 years. These outbreaks have been treated with topical application of the raw juice to the surface lesion. The severity and reoccurrence of the virus infection has been drastically reduced using this active agent.

Case 8

A 33-year old male was diagnosed as having genital herpes HSV type-2. Application of 1-3 drops of the active agent to the surface lesions twice a day significantly reduced the severity and discomfort, burning, and itching, and rapidly speeded up the healing process in 5 days or less.

Case 9

A 33-year old male was diagnosed as having genital herpes in 1984 with several reocurrences per year since. In 1988, the active ingredient was applied topically to the surface lesions. The outbreak dried up almost immediately and disappeared completely within 3 days. There was no pain involved during or after the application of liquid.

EXAMPLE 7

Treatment of Herpes Zoster

This example illustrates how the active antiviral agent of this invention is used for treatment of herpes zoster.

Patient having a severe facial trigeminal herpes zoster on his left cheek is treated with topical ointment formulation of 5% active ingredient obtained from the hull of the kukui nut in polyethylene glycol. The ointment is applied in thin layer over the strand of blisters and left to dry. After each washing of the face, a new thin layer is reapplied. The edema retreats, and within 24 hours blisters becoming crusty. Itching and pain almost completely disappears during 48 hours.

EXAMPLE 8

Treatment of Epithelial Keratitis

This example illustrates how the active agent of this invention is used for treatment of epithelial keratitis of the eye caused by herpes simplex virus type-1 and 2.

Sterile ophthalmic solution containing 1% of the kukui nut liquid as an active ingredient in an aqueous solution with acetic acid and sodium acetate, sodium chloride and a preservative thimerosal in amount of 0.001% is instilled into an eye of a patient suffering from primary keratoconjunctivitis in the following regimen: One drop of the 1% ophthalmic solution, as described above, is instilled onto the cornea of the affected eye every two hours for a maximum of 9 drops per day until the corneal ulcer reepithelized. The treatment is continued for another week with 1 drop every four hours with maximum dose of 5 drops per day. Complete reepithelization occurs in about 14 days of treatment.

EXAMPLE 9

Prevention of Scarring During Chickenpox

This example illustrates the use of the active ingredient of this invention in preventing scarring due to chickenpox infection.

A six year old girl having the face covered with ulcerous breakout due to chickenpox infection is administered topically an ointment containing 1% of the active ingredient in polyethylene glycol over the ulcerous breakout every time after washing the face. In one day, the breakout and sores dry out and at the end of the infection, there are no visible scars on the patient's face.

While only a few embodiments of the present invention are shown and described herein, it will be apparent to those skilled in this art that various modifications and changes can be made in the pharmaceutical use of the active ingredient present in the juice of the kukui nut green hull to cure viral infections, by topical or other application of the active ingredient without departing from the spirit and scope of this invention. All such modifications and changes coming within the scope of the appended claims are intended to be covered thereby.

What is claimed:

1. A method of treating topical lesions caused by topically manifested viral infection in mammal, which method comprises a topical administration to the surface of the lesions on the skin of the mammal of a topical pharmaceutical composition consisting essentially of 1-5% wt/wt active ingredient present in the juice of the green hull of the kukui nut *Aleurites moluccana*, wherein said active ingredient is formulated in a pharmaceutically acceptable carrier.

2. The method of claim 1 wherein the viral infection is herpes zoster.

3. The method of claim 1 wherein the viral infection is chickenpox.

4. A method of treating genital warts caused by virus in a mammal, which method comprises a topical application to the genital wart on the skin of the mammal, of a pharmaceutical composition consisting essentially of 1-5% wt/wt active antiviral ingredient present in the juice of the green hull of the kukui nut *Aleurites moluccana*, wherein said active ingredient is formulated in a pharmaceutically acceptable carrier.

* * * * *